United States Patent
Alroy et al.

(10) Patent No.: US 6,320,044 B1
(45) Date of Patent: Nov. 20, 2001

(54) PROCESS FOR RECOVERING LIPOPHILIC OLIGOSACCHARIDE ANTIBIOTICS

(75) Inventors: Yair Alroy, Parsippany; Steven Blaisdell, Jackson; Allan Morenberg; Schaefer Eugene, both of Westfield, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/454,454

(22) Filed: Dec. 6, 1999

Related U.S. Application Data

(60) Provisional application No. 60/112,891, filed on Dec. 18, 1998.

(51) Int. Cl.⁷ .............................. C07H 1/06; A61K 31/715
(52) U.S. Cl. ..................... 536/127; 536/123.1; 514/25; 514/54
(58) Field of Search .................. 536/127, 123.1; 514/25, 54

(56) References Cited

U.S. PATENT DOCUMENTS

| | | |
|---|---|---|
| 4,597,968 | 7/1986 | Castaldi et al. . |
| 4,735,903 | 4/1988 | Waitz et al. . |
| 5,624,914 | 4/1997 | Patel et al. . |
| 5,763,600 * | 6/1998 | Ganguly et al. ............ 536/113 |
| 5,776,912 * | 7/1998 | Patel et al. ............... 514/54 |
| 5,780,442 * | 7/1998 | Mierzwa et al. ............ 514/25 |

OTHER PUBLICATIONS

A.K. Ganguly et al., The Structure of New Oligosaccharide Antibiotics, 13–384 Components 1 and 5, Heterocycles, vol. 28, No. 1, (1989), pp. 83–88.

A.K. Ganguly et al., Chemical Modification of Everninomicins, The Journal of Antibiotics, vol. XXXV No. 5, (1982), pp. 561–570.

V. M. Girijavallabhan & A.K. Ganguly, Kirk–Othmer Encyclopedia of Chemical Technology, 4$^{th}$ Ed., vol. No. 3, (1992), pp. 259–266.

Derek E. Wright, Tetrahedron Report No. 62, The Orthosomycins a New Family of Antibiotics, Tetrahedron vol. 35, Pergamon Press Ltd., (1979), pp. 1207–1237.

* cited by examiner

*Primary Examiner*—Ralph Gitomer
*Assistant Examiner*—Devesh Khare
(74) *Attorney, Agent, or Firm*—Margaret M. Albanese; Joanne P. Will; Joseph T. Majka

(57) ABSTRACT

A process for recovering a lipophilic oligosaccharide antibiotic from an aqueous fermentation broth containing the lipophilic oligosaccharide antibiotic admixed with impurities, by-products and/or suspended solids, comprising:
   a) combining said fermentation broth with an adsorbent;
   b) adjusting the pH of the broth to alkaline in order to solubilize the antibiotic in the broth;
   c) allowing sufficient time for the solubilized antibiotic in the alkaline broth to be adsorbed by the adsorbent;
   d) adjusting the pH of the broth to about neutral in order to stabilize the antibiotic adsorbed on the adsorbent; and
   e) separating the adsorbent to which the antibiotic is adsorbed from the broth.

A medium for storing an oligosaccharide antibiotic comprising an adsorbent having a lipophilic oligosaccaride antibiotic adsorbed thereon is also disclosed.

19 Claims, No Drawings

PROCESS FOR RECOVERING LIPOPHILIC OLIGOSACCHARIDE ANTIBIOTICS

REFERENCE TO RELATED APPLICATIONS

The present application claims priority back to U.S. Provisional Application No. 60/112,891, filed on Dec. 18, 1998.

BACKGROUND

Orthosomycins are a group of complex lipophilic oligosaccharide antibiotics that are active against gram positive bacteria including methicillin resistant Staphylococci and/or vancomycin resistant Enterococci. Lipophilic oligosaccharide antibiotics include, for example, eveminomicins, the flambamycins, the avilamycins and the curamycins which contain at least one acidic phenolic hydrogen, at least one orthoester linkage associated with carbohydrate residues and usually a nitrogen-containing group. Lipophilic oligosaccharide antibiotics are components from fermented cultures of microorganisms. For example, certain everninomicin type compounds can be prepared from the fermentation of *Micromonospora carbonacea*. Various lipophilic oligosaccharide antibiotics and processes for their preparations are known and taught in U.S. Pat. Nos. 4,597,968, 4,735,903, 5,624,914 and 5,763,600; in A. K. Ganguly et al., The Structure of New Oligosaccharide Antibiotics, 13–384 Components 1 and 5, Heterocycles, Vol. 28, No. 1, (1989), pp. 83–88; in A. K. Ganguly et al., Chemical Modification of Everninomicins, The Journal of Antibiotics, Vol. XXXV No. 5, (1982), pp. 561–570; in V. M. Girijavallabhan & A. K. Ganguly, Kirk-Othmer Encyclopedia of Chemical Technology, 4th Ed., Vol. No. 3, (1992) pp. 259–266; in Derek E. Wright, Tetrahedron Report Number 62, The Orthosomycins a New Family of Antibiotics, Tetrahedron Vol. 35, Pergamon Press Ltd., (1979), pp 1207–1237; and in references cited therein. In addition to being complex in their molecular structures, these antibiotics are highly susceptible to degradation. These complex antibiotics are produced in fermentation broths, together with many impurities, precursors and by-products. Thus, the efficient separation of the antibiotic component from the fermentation broth is highly challenging. It would be highly desirable to provide a method which efficiently recovers the desired lipophilic oligosaccharide antibiotics (orthosomycins) from a fermentation broth or mixture wherein the antibiotics are admixed with other impurities, precursors and/or by-products.

SUMMARY OF THE INVENTION

During our studies with lipophilic oligosaccharide antibiotics, we have discovered an unexpectedly and surprisingly efficient method for recovering the desired lipophilic oligosaccharide antibiotics (orthosomycins) from a fermentation broth.

Accordingly, the present invention is directed toward a process for recovering a lipophilic oligosaccharide antibiotic from an aqueous fermentation broth containing the lipophilic oligosaccharide antibiotic admixed with impurities, by-products and/or suspended solids, comprising:

a) combining said fermentation broth with an adsorbent;

b) adjusting the pH of the broth to alkaline in order to solubilize the antibiotic in the broth;

c) allowing sufficient time for the solubilized antibiotic in the alkaline broth to be adsorbed by the adsorbent;

d) adjusting the pH of the broth to about neutral in order to stabilize the antibiotic adsorbed on the adsorbent; and e) separating the adsorbent to which the antibiotic is adsorbed from the broth.

In another embodiment, the present invention is directed towards a process for recovering a lipophilic oligosaccharide antibiotic from an aqueous fermentation broth containing the lipophilic oligosaccharide antibiotic admixed with impurities, by-products and/or suspended solids, comprising:

i) combining said broth with an adsorbent;

ii) adjusting the pH of the broth to alkaline in order to solubilize the antibiotic in the broth;

iii) allowing sufficient time for the solubilized antibiotic in the alkaline broth to be adsorbed by the adsorbent;

iv) separating the adsorbent to which the antibiotic is adsorbed from the broth; and v) washing the adsorbent to which the antibiotic is adsorbed with an aqueous wash having an acid pH such that the final pH of the wash-absorbent mixture is about neutral in order to stabilize the antibiotic.

Optionally, the fermentation broth can be pretreated prior to step a) or i), wherein said aqueous fermentation broth is pretreated by separating the suspended solids from the broth and resuspending the suspended solids in an aqueous medium of about neutral pH to provide said resuspended solids as the fermentation broth for subsequent treatment.

Optionally, the process can further comprise step f) or vi) separating the antibiotic from the adsorbent to which the antibiotic is adsorbed. Preferably the adsorbed antibiotic is separated from the adsorbent by eluting the adsorbent with an organic solvent.

Also, optionally the process can further comprise step g) or vii) separating the antibiotic from the organic solvent. Preferably, the lipophilic oligosaccharide antibiotic is of the Formula I:

Formula I

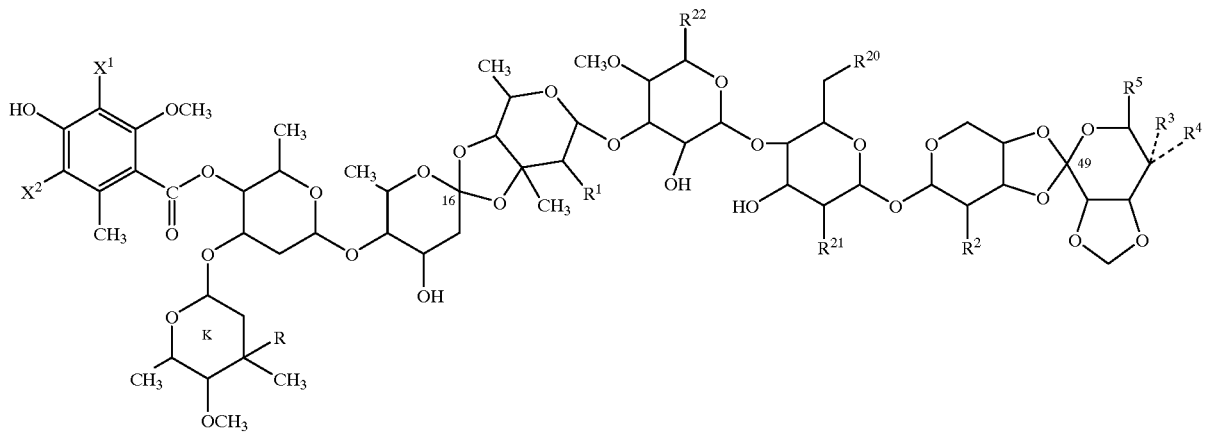

R = NO₂, NO, NHOH and/or NH₂

Also preferred is that the lipophilic oligosaccharide antibiotic of the Formula I has the stereoconfiguration of Formula I' (or Formula I" as shown in the Example which follows):

Formula I'

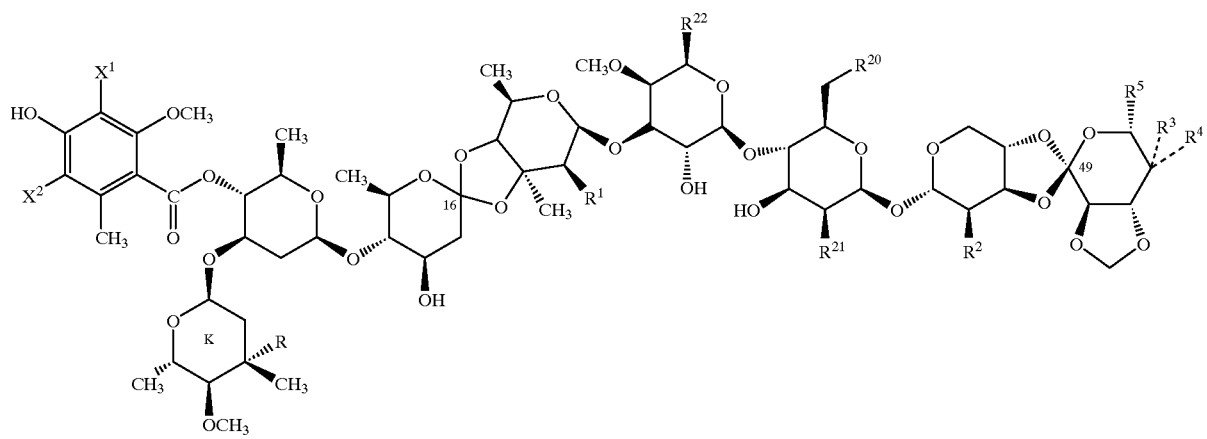

R = NO₂, NO, NHOH and/or NH₂ wherein (for either the lipophilic oligosaccharide antibiotic of formulas I or I'), $X^1$ and $X^2$ independently represent hydrogen (H) or chloro (—Cl), provided at least one of $X^1$ and $X^2$ is chloro;

Ring K is as shown or is hydrogen;

R is —NO₂, —NO, —NHOH and/or —NH₂, $R^1$ is hydrogen or —OH;

$R^2$ is —OH or —OR$^{12}$,
  wherein
    $R^{12}$ is alkyl or C(O)R$^{13}$ wherein R$^{13}$ is alkyl;

$R^3$ is hydrogen,

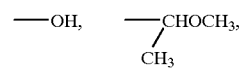

—C(O)R$^{14}$, —CH(OH)R$^{15}$ or

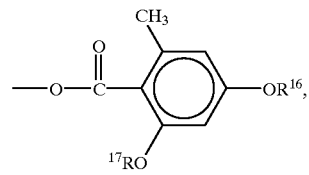

wherein $R^{14}$ is hydrogen or alkyl,
$R^{15}$ is alkyl,
$R^{16}$ is hydrogen, alkyl or alkenyl,
$R^{17}$ is hydrogen, alkyl or alkenyl,
$R^4$ is hydrogen or OH;
$R^5$ is hydrogen or methyl;
$R^{20}$ is —OH or —OCH$_3$;
$R^{21}$ is —OH or —OCH$_3$; and
$R^{22}$ is hydrogen, —CH$_3$ or —CH$_2$OH.

The dashed line indicates a bond whose stereochemistry can be either in the R or S stereoconfiguration. Preferably, $X^1$ and $X^2$ are chloro. Preferably, $R^1$ is hydrogen or —OH. Also preferred is that $R^2$ is —OH, —OCH$_3$ or —OCH$_2$CH$_2$OH. Preferably $R^3$ is

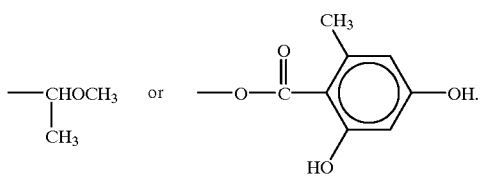

Also preferred is that $R^4$ is hydrogen. Preferably, $R^5$ is hydrogen. Also preferred is that $R^{20}$ and $R^{21}$ are —OCH$_3$ and $R^{22}$ is —CH$_3$. Preferably, $R^3$ in oligosaccharide antibiotic of formula I and I' has the ▰ stereoconfiguration.

In another embodiment, the present invention is directed toward a medium for storing an oligosaccharide antibiotic comprising an adsorbent having a lipophilic oligosaccharide antibiotic adsorbed thereon. Preferably the lipophilic oligosaccharide antibiotic is of formula I, more preferably of formula I' or I" as shown in the Example which follows. Preferably, the adsorbent is an insoluble material that is capable of adsorbing a lipophilic oligosaccharide antibiotic from an alkaline aqueous solution or suspension, and releasing the antibiotic into an eluting organic solvent. Also preferred is that the adsorbent is polymeric. Also preferred is that the polymeric adsorbent is comprised of a nonionic, polymeric matrix. More preferably, the adsorbent is comprised of a nonionic, polymeric matrix in which the polymer phase of the matrix is an aliphatic, crosslinked polymer. Also preferred is that the aliphatic, cross-linked polymer has a macroreticular structure, which, together with the aliphatic nature of its surface, imparts adsorptive properties to the adsorbent. Most preferably, the aliphatic, crosslinked polymer is an acrylic.

One advantage of the present invention is that it provides a process for efficiently recovering a lipophilic oligosaccharide antibiotic from a fermentation broth in yields as high or even higher than in other known processes.

A second advantage of the present invention is that it provides a process that is more environmentally acceptable than other known processes. The present process avoids contamination of the whole fermentation broth or resuspended solids therefrom, compared with processes that employ direct extraction of a whole fermentation broth or resuspended solids therefrom with organic solvents which otherwise create a large volume of waste that must be disposed of.

A third advantage of the present invention is that it provides a process for recovering a lipophilic oligosaccharide antibiotic from a fermentation broth that avoids the expensive handling of large volumes of organic solvents, since only a small amount of solvent can be used for elution and/or regeneration of the adsorbent.

A fourths advantage of the present invention is that it provides a process for recovering a lipophilic oligosaccharide antibiotic from a fermentation broth which avoids the formation of an emulsion formed by water/organic solvents mixtures which otherwise would require expensive centrifugation equipment for separation.

A fifth advantage of the present invention is that it provides a process for recovering a lipophilic oligosaccharide antibiotic from a fermentation broth that is less expensive to operate than other known processes.

A sixth advantage of the present invention is that it provides a process for recovering a lipophilic oligosaccharide antibiotic from a fermentation broth that can conveniently be employed either in a batch mode or in a continuous or semi-continuous mode such as in a column.

A seventh advantage of the present invention is that it provides a medium for retaining an unpurified oligosaccharide antibiotic following separation of the adsorbent to which the antibiotic is adsorbed from the fermentation broth or acid wash. The adsorbent with the adsorbed antibiotic can be stored without loss of the antibiotic. This medium enables the process to be interrupted in order to attend to or accommodate other production functions, i.e. maintenance, personnel scheduling and the like.

DETAILED DESCRIPTION OF THE INVENTION

The following terms are used as defined below unless otherwise indicated: ▰ or ▱ indicates the stereoconfiguration of an enantiomer, as described, for example, in J. March, Advanced Organic Chemistry, Third Edition, John Wiley and Sons, New York, 1985, 1346 pages; ⋯ indicates a bond whose stereochemistry can be either in the R or S stereoconfiguration;

alkyl—represents straight and branched carbon chains and contains from one to six carbon atoms (i.e. $C_1$–$C_6$); for example methyl, ethyl, propyl, iso-propyl, n-butyl, n-pentyl, isopentyl, hexyl and the like.

alkenyl—represents straight and branched carbon chains having at least one carbon to carbon double bond and containing from 2 to 12 carbon atoms, preferably from 2 to 6 carbon atoms and most preferably from 3 to 6 carbon atoms.

The terms "lipophilic oligosaccharide antibiotic," "oligosaccharide antibiotic" and "orthosomycin" are considered substantially synonymous, and refer to a group of complex lipophilic oligosaccharide antibiotics ("antibiotic") including, for example, everninomicins, the flambamycins, the avilamycins and the curamycins, that contain at least one acidic phenolic hydrogen, at least one orthoester linkage associated with carbohydrate residues (preferably two orthoester linkages, typically at carbon numbers 16 and 49, i.e. (C16) and (C49)) and usually a nitrogen-containing group, such as nitro, nitroso, hydroxyamino or amino.

The fermentation broth is the aqueous liquid (water-containing) in which the microorganism is cultivated or grown to produce the desired lipophilic oligosaccharide antibiotic. At the end of cultivation, the liquid broth contains many impurities, by-products and/or suspended solids mixed or associated with the lipophilic oligosaccharide antibiotic(s). At that time, the pH of the broth is typically neutral (i.e. between about 6 and 8). U.S. Pat. No. 4,597,968 teaches examples of various growth media for the production of a lipophilic oligosaccharide antibiotic. To prepare the compound of formula I" as shown in the Example which follows, the cultivation process can utilize a strain of

*Micromonospora carbonacea var africana*, which produces an everninomicin complex consisting of three forms of everninomicin: nitro (R=NO$_2$), nitroso (R=NO), and hydroxylamine (R=NHOH), of which the nitro form is preferred for therapeutic purposes.

Optionally, the fermentation broth can also refer to a suspension made of the suspended solids contained therein and the lipophilic oligosaccharide antibiotic(s) associated with the suspended solids. Such suspension can be prepared by pretreatment of the aqueous fermentation broth, in which suspended solids and lipophilic oligosaccharide antibiotic(s) associated therewith are separated from the broth and are subsequently resuspended in an aqueous medium of about neutral pH. The suspended solids and lipophilic oligosaccharide antibiotic(s) associated therewith in the fermentation broth can be separated, for example, by screening, filtration, centrifugation and the like, and resuspended in an aqueous medium for subsequent combining with, adding to or processing with the adsorbent.

At the end of cultivation or at harvest, typically the fermentation broth is cooled to reduce degradation of the lipophilic oligosaccharide antibiotic in the broth, usually to a temperature ranging from about 2° C. to about 25° C. The broth can be cooled in the vessel by means of internal cooling coils or an external cooling jacket. Alternatively, the broth can be cooled by passing it through a heat exchanger. Where cooling equipment is not available, the broth can be allowed to cool to the ambient temperature.

Following cooling, the broth is combined with the adsorbent. For example, the broth can be transferred to an adsorption tank where the resin has been added. Alternatively, the adsorbent can be added to the broth.

The adsorbent is an insoluble material that is capable of a) adsorbing one or more lipophilic oligosaccharide antibiotic(s) from an alkaline aqueous solution or suspension, and b) releasing the adsorbed lipophilic oligosaccharide antibiotic into an eluting organic solvent having a suitable polarity or an eluting salt/buffer solution. Such organic solvents include, for example, ethyl acetate and isopropyl acetate. The adsorbent can be made of natural or synthetic materials. Preferably, the adsorbent is a polymeric adsorbent. Also preferred is that the polymeric adsorbent is a nonionic, polymeric matrix which derives its adsorptive properties from (a) its macroreticular structure (an intricate matrix containing both a continuous polymer phase and a continuous pore phase) and (b) the aliphatic nature of its surface, both of which contribute to the adsorption of the lipophilic oligosaccharide antibiotic. Inherent to the macroreticular structure is the high surface to volume ratio and rapid mass transfer of the antibiotic during adsorption. More preferably, the polymer phase of the matrix is an aliphatic, crosslinked polymer, more preferably an acrylic, crosslinked polymer. A commercially available polymeric adsorbent is Amberlite® XAD-7 (HP) polymeric adsorbent, which is available as white insoluble beads. Amberlite® (trademark of the Rohm and Haas Company, Philadelphia, Pa.) XAD-7 polymeric adsorbent has a surface area of at least 400 m$^2$/g and a porosity of at least 50% (volume/volume). Processes for preparing the polymeric adsorbent can be found in U.S. Pat. No. 4,297,220, whose preparative teachings are incorporated herein by reference. The pore size range of this polymeric adsorbent is about 1 to about 650 Angstroms. The amount of polymeric adsorbent to be employed can range from about 10 mL to about 100 mL hydrated polymeric adsorbent per gram of lipophilic oligosaccharide antibiotic, preferably from about 30 to about 80 mL, more preferably from about 50 to about 60 mL hydrated polymeric adsorbent.

Following separation or elution of the antibiotic from the resin with organic solvent, the adsorbent can be regenerated to its desired aqueous or hydrated form by following the recommendations of the manufacturer of the adsorbent. For example, the adsorbent from which the lipophilic oligosaccharide antibiotic has been separated, can be regenerated by washing the adsorbent with a polar solvent such as ethanol or methanol, followed by washing the adsorbent with water. The regenerated adsorbent can be reused for subsequent adsorption of the lipophilic oligosaccharide antibiotic.

Alternatively, the adsorbent can also be an anion exchange resin. An anion exchange resin is a stable, insoluble matrix which has an affinity for negatively charged ions, i.e. hydroxide or chloride. The anion exchange resin can be "strong" or "weak." Strong anion exchange resins can preferably possess a quaternary ammonium group (–N+ R$^{10}$R$^{11}$R$^{12}$R$^{13}$X$^-$ where R$^{10}$, R$^{11}$, R$^{12}$ and R$^{13}$ each can be an alkyl group and X$^-$ is a counteranion), whereas a weak anion exchange resin preferably possesses a primary, secondary or tertiary amine group. One with ordinary skill in the art can determine the volume of resin needed to capture or adsorb the lipophilic oliogosaccardide antibiotic by performing laboratory scale adsorption experiments, the results of which are affected by the amount of antibiotic in the fermentation broth, the ionic exchange capacity of the anion exchange resin, the amount of impurities in the fermentation broth and the desired flow rate. Generally, resins with higher anionic exchange capacity are preferred over resins with a lower exchange anionic capacity. One commercially available strong anion exchange resin is Amberlite® IRA-958 (trademark of Rohm & Haas Co., Philadelphia, Pa., USA), characterized as a macroreticular, strongly basic anion exchange resin (OH— or hydroxide cycle) with a crosslinked, acrylic copolymer structure produced in the form of spherical particles. Another anion exchange resin is Amberlite® IRA-743 resin, supplied as fully hydrated spherical particles. A commercially available weak anion exchange resin is known as BioRex 5 (available from Bio-Rad Laboratories, Life Science Group, Hercules, Calif.) characterized as having a styrene divinylbenzene backbone, commercially available as 75–150 micron and 45–75 micron beads. Another weak anion exchange resin is DEAE-cellulose. The lipophilic oligosaccharide antibiotic can be eluted from the anion exchange resin by treating the resin with a salt/buffer solution. The salt/buffer solution can contain one or more salts, one or more organic solvents and/or water to provide a buffer solution having a pH between about neutral and alkaline. Suitable salts can include ammonium chloride, sodium or potassium bicarbonate and sodium or potassium carbonate and the like. Suitable organic solvents can include methanol, ethyl acetate, isopropyl acetate and the like. A suitable eluting salt/buffer solution can be, for example, a buffer made of 0.25 M ammonium chloride (NH$_4$Cl) in a solvent mixture having 2 parts methanol, 1 part water and 1 part ethyl acetate. Following separation of the lipophilic oliosaccharide antibiotic from the anionic exchange resin, the resin can be regenerated by treatment with a dilute solution of a base, e.g. 4 bed volumes of 5% sodium hydroxide, followed by multiple washings with deionized water.

The pH of the broth can be adjusted to alkaline by stepwise or gradual addition of a base to solubilize the antibiotic in the broth, thereby promoting adsorption of the antibiotic to the adsorbent. Suitable bases for making the broth alkaline include, for example, hydroxides, carbonates and bicarbonates of alkali and alkaline earth metals, such as sodium hydroxide, calcium hydroxide, calcium carbonate, cesium carbonate, sodium bicarbonate, potassium bicarbonate and lithium bicarbonate. Preferably, the base is added as a dilute solution in order to minimize the chemical degradation of the antibiotic with concentrated portions of alkali. Such dilute solutions can include, for example, a concentration of less than 1 Normal (N) of base, preferably less than 0.5 N of base. Preferably, the pH is adjusted with a base to a pH between about 9 and 11.

Sufficient time should be allowed for the solubilized antibiotic in the alkaline broth to be adsorbed by the adsorbent, typically between about 1 to about 24 hours or more, preferably between about 3 to 6 hours or more. Preferably, the broth containing the adsorbent is agitated to promote or facilitate adsorption of the solubilized antibiotic onto the adsorbent. Such agitation can be accomplished, for example, by stirring or mixing the broth together with the adsorbent. Additionally, the broth can be agitated during any one, two, three, four, five or all of the other steps in the process to facilitate mixing of the ingredients, e.g. incorporation of the base to adjust the pH.

Also, where desired, the broth may be aerated during any one, two, three, four, five or all of the steps in the process to promote oxidation of the antibiotic to the more oxidized forms (i.e. —NO form and preferably —$NO_2$). Preferably, the broth is aerated when or while the pH of the broth is alkaline. Such aeration can be effected, for example, by sparging or passing air through the broth while maintaining agitation. The level of dissolved oxygen in the broth may be used to gauge the effectiveness of the aeration. The concentration of dissolved oxygen should be sufficiently high to promote oxidation of the lipophilic oligosaccharide antibiotic complex toward the R=—NO form and/or the preferred —$NO_2$. The concentration of dissolved oxygen may be determined using a dissolved oxygen probe.

When the desired lipophilic oligosaccharide antibiotic has been adsorbed onto the adsorbent, the pH of the broth containing the adsorbent can be reduced to a pH of about neutral, by stepwise or gradual addition of an acid, as in step (d), to reduce the solubility of the lipophilic oligosaccharide antibiotic in the broth and/or to stabilize the antibiotic on the adsorbent. Alternatively, the pH of the adsorbent to which the antibiotic is adsorbed is adjusted to neutral with an acid wash, as in step v). By "stabilizing" is meant chemically stabilizing the antibiotic from degradation and/or enhancing the chemical affinity or strength of attachment of the antibiotic to the adsorbent. Preferably, the pH of the broth is lowered stepwise or gradually so as to minimize degradation of the antibiotic with concentrated portions of acid. Suitable acids for reducing the pH of the broth from alkaline to about neutral include mineral acids such as sulfuric, hydrochloric, phosphoric, boric and the like, mineral salts such as sodium phosphate monobasic, potassium phosphate monobasic, and the like, as well as organic acids such as formic or acetic acid. Preferably the acid is added as a dilute solution such as, for example, at a concentration of less than 1 N acid, more preferably less than 0.5 N acid. The pH can be adjusted with acid to a pH between about 6 and 8. Preferably the pH is adjusted to a pH between about 6.5 to 7.5.

After the pH of the broth is adjusted to neutral, the adsorbent with the adsorbed antibiotic (the adsorbate) can be separated from the broth using, filtration, screening, sedimentation andlor decantation procedures and the like. For example, the adsorbate can be screened out from the spent broth using a vibrating screen. Optionally and preferably, the adsorbate can be washed with clean water, the temperature of which can range from about 2° C. to about 25° C. until the wash water is nearly clear. The adsorbate can be stored at a temperature less than 15° C. Preferably the temperature can range from about −20° C. to about 12° C., more preferably from 4° C. to about 8° C. for 2 months or more. This allows the process to be temporarily interrupted in order to prepare for additional processing steps.

It should be noted that the sequence of steps a) and b) or i) and ii) are interchangeable. Preferably though, step a) precedes step b) and step i) precedes step ii).

Optionally, in step f) or vi), the adsorbed lipophilic oligosaccharide antibiotic can be separated or removed from the adsorbent. Such separation or removal can be effected by packing the adsorbate into a column and eluting the lipophilic oligosaccharide antibiotic from the adsorbate using an organic solvent having a suitable polarity, such as ethyl acetate or isopropyl acetate. The term "suitable polarity" refers to a polarity that is sufficient to elute the antibiotic from the adsorbent while leaving a substantial portion of the impurities on the adsorbent. The amount of organic solvent can range from about one to about ten parts solvent per one volume of hydrated polymer adsorbent, preferably about 2 to about 4 volumes organic solvent. Essentially, the organic solvent passing through the column elutes the adsorbed antibiotic from the adsorbate.

Optionally, in step g) or vii), the antibiotic is separated from the organic solvent. Such separation of the antibiotic from the organic solvent can be effected by evaporating the organic solvent to dryness, yielding the desired lipophilic oligosaccharide antibiotic in a dried, partially purified form. Alternatively, the antibiotic may be separated from the organic solvent after a subsequent or later processing step. such as purification, oxidation, etc. as needed.

EXAMPLE

Process for recovering a lipophilic oligosaccharide antibiotic from an aqueous fermentation broth Formula I″

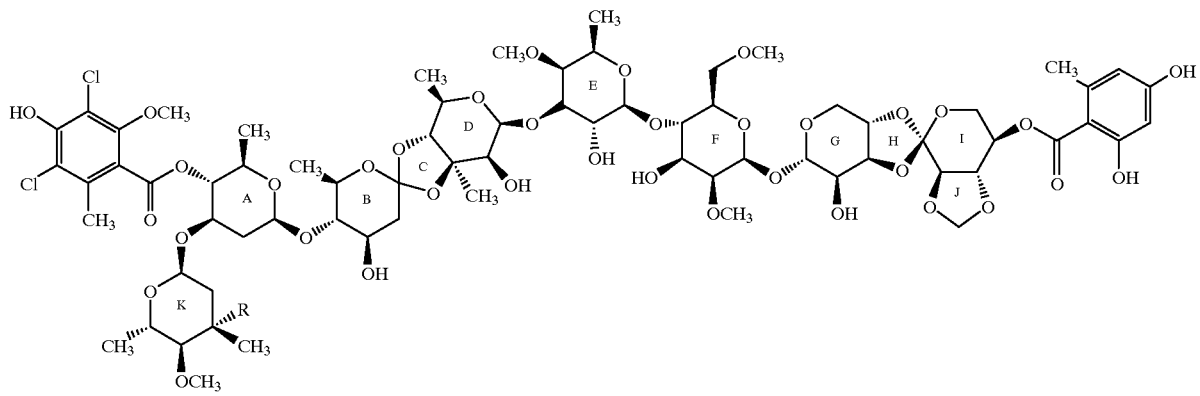

R = NHOH, NO and/or NO$_2$

An aqueous fermentation broth is prepared by propagating the microorganism *Micromonospora carbonacea var africana* in a 10,000 liter (L) fermentation vessel containing water and other nutrients for growth. During fermentation, the microorganism produces a complex of lipophilic oligosaccharide antibiotics known as everninomicins, including variable combinations of the following three forms: the hydroxylamine form (R=NHOH), the nitroso form (R=NO) and the nitro form (R=NO$_2$). At harvest, the fermentation broth is chilled to 15° C., and aerated under agitation. The chilled, aerated broth is transferred to a mixing tank containing about 56 mL of hydrated Amberlite XAD-7 (grade HP), an adsorbent, per gram of everninomicin complex. During transfer, the broth is kept chilled (15° C.), agitated and aerated to maintain the dissolved oxygen above 30%. The pH is adjusted to 10.5 by gradual addition of 0.4 N NaOH and is maintained for 30 minutes. After this time, the pH is adjusted to 9.2 using 0.2 N H$_2$SO$_4$ and is maintained for 3.5 hours. After completion of the 3.5 h hold period, the pH is adjusted to 7.0 by gradual addition of 0.2 N H$_2$SO$_4$. The adsorbate is screened out from the spent broth using a vibrating screen, and it is washed repeatedly with cold, soft water until the wash water is essentially clear. The washed adsorbate is packed in a column and the everninomicin complex is eluted from the adsorbate using three volumes of isopropyl acetate per one volume of hydrated adsorbent. The isopropyl acetate is subsequently evaporated to yield the bulk antibiotic drug of Formula I″.

PREPARATION OF STARTING MATERIALS Lipophilic oligosaccharide antibiotics, i.e. of formulas I, I′ and I″ are known in the art and/or can be prepared using known methods, such as taught, for example, in U.S. Pat. Nos. 4,597,968, 4,735,903, 5,624,914, 5,763,600; in A. K. Ganguly et al., The Structure of New Oligosaccharide Antibiotics, 13–384 Components 1 and 5, Heterocycles, Vol; 28, No. 1, (1989), pp. 83–88; in A. K. Ganguly et al., Chemical Modification of Everninomicins, The Journal of Antibiotics, Vol. XXXV No. 5, (1982), pp. 561–570; in V. M. Girijavallabhan & A. K. Ganguly, Kirk-Othmer Encyclopedia of Chemical Technology, 4th Ed., Vol. No. 3, (1992) pp. 259–266; in Derek E. Wright, Tetrahedron Report Number 62, The Orthosomycins a New Family of Antibiotics, Tetrahedron Vol. 35, Pergamon Press Ltd., (1979), pp. 1207–1237; in A. Saksena et. al., Structure Elucidation of SCH49088, A Novel Everninomicin Antibiotic Containing An Unusual Hydroxylamino-ether Sugar, Everhydroxylaminose, Tetrahedron Letters, 39 (1998), pages 8441–8444; and in references cited therein. Everninomicin-type antibiotics are components from cultures of microorganisms such *Micromonospora carbonaceae*. For example, certain everninomicin type compounds of formula I″ can be prepared from typical fermentation of *Micromonospora carbonacea var. africana*, NRRL 15099, ATCC39149 or higher yielding subspecies therof. For example, one subspecies, strain PF6-3, is prepared from the parent strain ATCC39149, by reisolations and treatments with ultraviolet light (UV) and N-methyl-N′-nitro-N-nitrosoguanidine (MNNG or NTG). Flambamycins are produced by *Streptomyces hygroscopicus*. Curamycin A is the primary component in the culture of *Streptomyces curacoi*. Avilamycins are the primary components produced by the bacterium *Streptomyces viridochromgenes*.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A process for recovering a lipophilic oligosaccharide antibiotic from an aqueous fermentation broth containing the lipophilic oligosaccharide antibiotic admixed with impurities, by-products and/or suspended solids, comprising:

a) combining said fermentation broth with an adsorbent;

b) adjusting the pH of the broth to alkaline in order to solubilize the antibiotic in the broth;

c) allowing sufficient time for the solubilized antibiotic in the alkaline broth to be adsorbed by the adsorbent;

d) adjusting the pH of the broth to about neutral in order to stabilize the antibiotic adsorbed on the adsorbent; and e) separating the adsorbent to which the antibiotic is adsorbed from the broth.

2. The process of claim 1 wherein the lipophilic oligosaccharide antibiotic is of Formula I:

Formula I

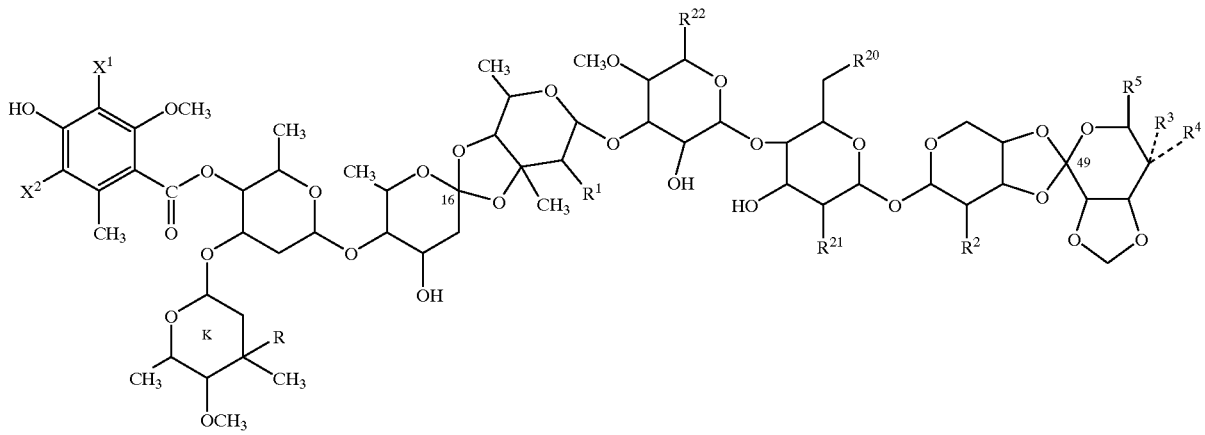

wherein $X^1$ and $X^2$ independently represent hydrogen or chloro, provided at least one of of $X^1$ and $X^2$ is chloro;

Ring K is as shown or is hydrogen;

R is —$NO_2$, —NO, —NHOH and/or —$NH_2$, $R^1$ is hydrogen or —OH;

$R^2$ is —OH or —$OR^{12}$,
  wherein
  $R^{12}$ is alkyl or $C(O)R^{13}$ wherein $R^{13}$ is alkyl;

$R^3$ is hydrogen,

—$C(O)R^{14}$, —$CH(OH)R^{15}$ or wherein
$R^{14}$ is hydrogen or alkyl,
$R^{15}$ is alkyl,
$R^{16}$ is hydrogen, alkyl or alkenyl,
$R^{17}$ is hydrogen, alkyl or alkenyl,
$R^4$ is hydrogen or OH;
$R^5$ is hydrogen or methyl;
$R^{20}$ is —OH or —$OCH_3$;
$R^{21}$ is —OH or —$OCH_3$; and
$R^{22}$ is hydrogen, —$CH_3$ or —$CH_2OH$.

3. The process of claim 1 wherein the lipophilic oligosaccharide antibiotic is of Formula I':

Formula I'

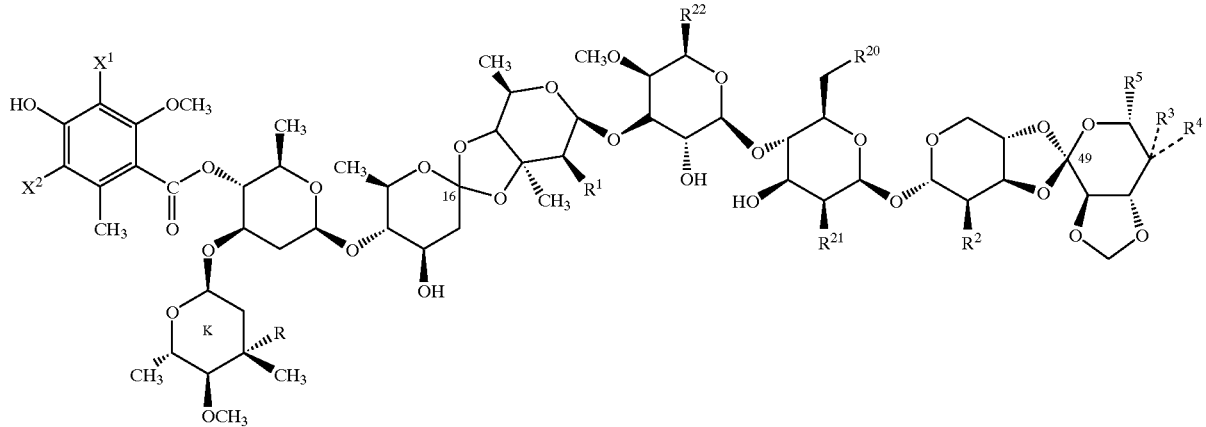

wherein
X$^1$ and X$^2$ independently represent hydrogen or chloro, provided at least one of of X$^1$ and X$^2$ is chloro;
Ring K is as shown or is hydrogen;
R is —NO$_2$, —NO, —NHOH and/or —NH$_2$,
R$^1$ is hydrogen or —OH;
R$^2$ is —OH or —OR$^{12}$,
   wherein
   R$^{12}$ is alkyl or C(O)R$^{13}$ wherein R$^{13}$ is alkyl;
R$^3$ is hydrogen,

—C(O)R$^{14}$, —CH(OH)R$^{15}$ or

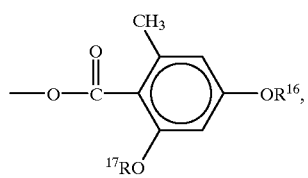

wherein
R$^{14}$ is hydrogen or alkyl,
R$^{15}$ is alkyl,
R$^{16}$ is hydrogen, alkyl or alkenyl,
R$^{17}$ is hydrogen, alkyl or alkenyl,
R$^4$ is hydrogen or OH;
R$^5$ is hydrogen or methyl;
R$^{20}$ is —OH or —OCH$_3$;
R$^{21}$ is —OH or —OCH$_3$; and
R$^{22}$ is hydrogen, —CH$_3$ or —CH$_2$OH.

4. The process of claim 1 wherein the lipophilic oligosaccharide antibiotic is of Formula I":

6. The process of claim 5, further comprising step f) separating the antibiotic from the adsorbent.

7. The process of claim 1 wherein the adsorbent is an insoluble material that is capable of adsorbing a lipophilic oligosaccharide antibiotic from an alkaline aqueous solution or suspension, and releasing the antibiotic into an eluting organic solvent.

8. The process of claim 1 wherein in step a) the adsorbent is polymeric.

9. The process of claim 1 wherein in step a), said absorbent is comprised of a nonionic, polymeric matrix.

10. The process of claim 1 wherein in step a), said absorbent is comprised of a nonionic, polymeric matrix in which the polymer phase of the matrix is an aliphatic, crosslinked polymer.

11. The process of claim 1 wherein in step a), said adsorbent is comprised of a nonionic, polymeric matrix in which the polymer phase of the matrix is an aliphatic, cross-linked polymer that has a macroreticular structure, which, together with the aliphatic nature of its surface, imparts adsorptive properties to the adsorbent.

12. The process of claim 1 wherein in step a), said adsorbent is comprised of a nonionic, polymeric matrix in which the polymer phase of the matrix is an aliphatic, cross-linked polymer that is an acrylic.

13. The process of claim 1 wherein in step a), said absorbent is comprised of a nonionic, polymeric matrix in which the polymer phase of the matrix is an acrylic, crosslinked polymer.

14. The process of claim 1 wherein in step b), said fermentation broth is adjusted to a pH between about nine and eleven in order to solubilize the antibiotic in the broth.

15. The process of claim 1 wherein in step c) said agitation to promote adsorption of the solubilized antibiotic onto the adsorbent is effected by stirring or mixing the broth and the adsorbent.

16. The process of claim 1 wherein in step d) said fermentation broth is adjusted to a pH between about six and eight in order to stabilize the antibiotic adsorbed on the adsorbent.

17. The process of claim 1, further comprising step f) separating the antibiotic from the adsorbent.

Formula I"

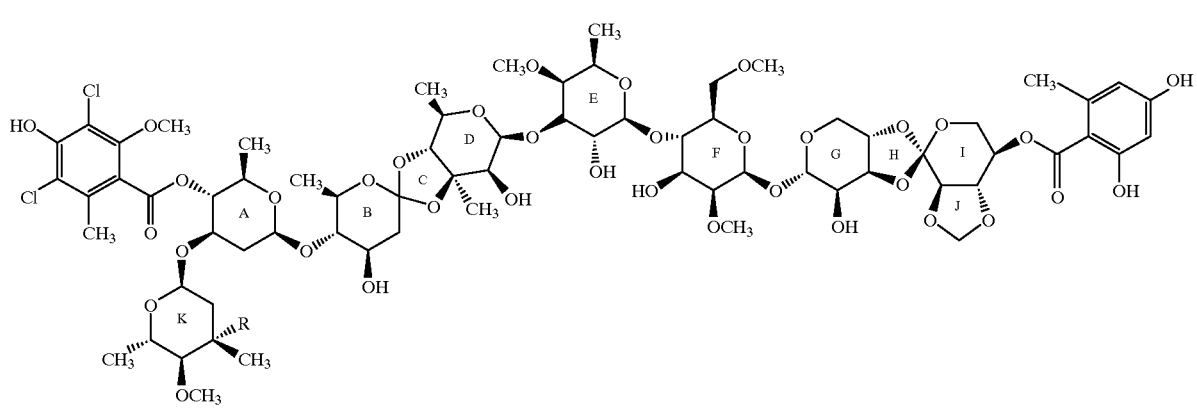

wherein R=—NO$_2$, —NO and/or —NHOH.

5. The process of claim 1 wherein prior to step a), said aqueous fermentation broth is pretreated by separating the suspended solids from the broth and resuspending the suspended solids in an aqueous medium to provide said resuspended solids as the fermentation broth for subsequent treatment.

18. The process of claim 17, wherein the antibiotic is separated from the adsorbent by elution with an organic solvent.

19. The process of claim 18, wherein the eluting organic solvent is ethyl acetate or isopropyl acetate.

* * * * *